United States Patent
Crespo Rodriguez et al.

(10) Patent No.: US 11,249,093 B2
(45) Date of Patent: Feb. 15, 2022

(54) METHODS FOR DETECTION OF TAU PROTEIN AGGREGATION MODULATING COMPOUNDS

(71) Applicant: JANSSEN VACCINES & PREVENTION B.V., Leiden (NL)

(72) Inventors: Rosa Crespo Rodriguez, The Hague (NL); Constantin Adrian Apetri, Noordwijkerhout (NL)

(73) Assignee: Janssen Vaccines & Prevention B.V., Leiden (NL)

(*) Notice: Subject to any disclaimer, the term of this patent is extended or adjusted under 35 U.S.C. 154(b) by 70 days.

(21) Appl. No.: 16/495,352

(22) PCT Filed: Mar. 27, 2018

(86) PCT No.: PCT/EP2018/057781
§ 371 (c)(1),
(2) Date: Sep. 18, 2019

(87) PCT Pub. No.: WO2018/178080
PCT Pub. Date: Oct. 4, 2018

(65) Prior Publication Data
US 2020/0025777 A1  Jan. 23, 2020

(30) Foreign Application Priority Data
Mar. 28, 2017 (EP) .................. 17163426

(51) Int. Cl.
*G01N 33/68* (2006.01)
*C07K 14/47* (2006.01)

(52) U.S. Cl.
CPC ...... *G01N 33/6896* (2013.01); *C07K 14/4711* (2013.01)

(58) Field of Classification Search
None
See application file for complete search history.

(56) References Cited

U.S. PATENT DOCUMENTS

| | | |
|---|---|---|
| 2002/0197737 A1 | 12/2002 | Mandelkow et al. |
| 2007/0218491 A1 | 9/2007 | Vasan et al. |
| 2013/0337463 A1* | 12/2013 | Brunden ............ G01N 33/6896 435/6.13 |
| 2013/0338202 A1* | 12/2013 | Esposito ............ C07D 263/56 514/374 |
| 2019/0029977 A1* | 1/2019 | Zankel ............... A61K 31/4035 |
| 2021/0238242 A1* | 8/2021 | Lashuel ............ G01N 33/6896 |

OTHER PUBLICATIONS

Sciencing "How to convert from CPM to Hertz" accessed from sciencing.com on Feb. 23, 2021 (Year: 2021).*

(Continued)

*Primary Examiner* — Adam Weidner
(74) *Attorney, Agent, or Firm* — Kramer Amado, PC

(57) ABSTRACT

The present invention provides a method for the in vitro formation and/or detection of paired helical filaments (PHF) of Tau protein, comprising incubating a mixture comprising a Tau protein preparation and a polyanionic co-factor for a pre-determined period of time under conditions that promote the formation of PHFs.

20 Claims, 11 Drawing Sheets

(56) References Cited

OTHER PUBLICATIONS

Usenovic "Internalized Tau Oligomers Cause Neurodegeneration by Inducing Accumulation of Pathogenic Tau in Human Neurons Derived from Induced Pluripotent Stem Cells" The Journal of Neuroscience, Oct. 21, 2015 • 35(42):14234-14250 (Year: 2015).*

Lim "Electronic Supplementary Information (ESI) Development of BODIPY-based fluorescent probe for imaging pathological tau aggregates in live cells" J. Name., 2013, 00, 1-3 | 1 (Year: 2013).*

Barghorn, et al., "Toward a Unified Scheme for the Aggregation of Tau into Alzheimer Paired Helical Filaments", Biochemistry, vol. 41, No. 50, pp. 14885-14896. (Dec. 1, 2002).

Friedhoff, et al., "Rapid Assembly of Alzheimer-like Paired Helical Filaments from Microtuble-Associated Protein Tau Monitored by Fluorescence in Solution", Biochemistry, vol. 37, No. 28, pp. 10223-10230. (Jul. 1, 1998).

Goedert, et al., "Assembly of microtubule-associated protein tau into Alzheimer-like filaments induced by sulphated glycosaminoglycans", Nature, MacMillan Journals Ltd., ETC, vol. 383, No. 6600, pp. 550-553. (Jan. 1, 1996).

Jeganathan, et al., "The Natively Unfolded Character of Tau and Its Aggregation to Alzheimer-like Paired Helical Filaments", Biochemistry, vol. 47, No. 4, pp. 10526-10539. (Oct. 7, 2008).

Perez, et al., "Polymerization of Tau into Filaments in the Presence of Heparin: The Minimal Sequence Required for Tau-Tau Interaction", Journal of Neurochemistry, Wiley Interscience, NY, NY, vol. 67, No. 3, pp. 1183-1190. (Sep. 1, 1996).

Yao, et al., "Aggregation Analysis of the Microtubule Binding Domain in Tau Protein by Spectroscopic Methods", Journal of Biochemistry, vol. 134, No. 1, pp. 91-99. (Jan. 1, 2003).

Morozova, et al. "Conformational Features of Tau Fibrils from Alzheimer's Disease Brain Are Faithfully Propagated by Unmodified Recombinant Protein", Biochemstry, 52, pp. 6960-6967. (2013).

* cited by examiner

A

B

METHODS FOR DETECTION OF TAU PROTEIN AGGREGATION MODULATING COMPOUNDS

FIELD OF THE INVENTION

The present invention relates to novel methods for the in vitro formation and detection of paired helical filaments (PHF) of Tau. These methods can be used for the selection of compounds capable of modulating, e.g. inhibiting pathological Tau-Tau protein association and pathological neurofilament aggregation. The methods of the present invention are particularly useful in screening compounds for the prophylaxis and treatment of Alzheimer's disease (AD).

BACKGROUND OF THE INVENTION

Dementia is a syndrome that can be caused by a number of progressive disorders that affect memory, thinking, behavior and the ability to perform everyday activities. About 36 million people worldwide are suffering from dementia today. The number of people with dementia is projected to double by 2030, and more than triple to 115.4 million people by 2050.

Alzheimer's disease (AD) is the most common type of dementia. Currently, one in nine people of age 65 and older (11 percent) and nearly half of those over age 85 have Alzheimer's disease. According to Alzheimer's Disease International, the current global costs of caring for these patients exceeds $600 billion annually. These costs are likely to rise even faster than the prevalence of disease, especially in the developing world, as more formal social care systems emerge, and rising incomes lead to higher opportunity costs.

AD is characterized by two pathological protein deposits in the brains of affected individuals, i.e. the amyloid plaques, consisting largely of amyloid fibers assembled from the beta amyloid (Aβ) peptide (a derivative of the amyloid precursor protein, APP) and the neurofibrillary tangles (NFT). NFT are formed by hyperphosphorylation of a microtubule-associated protein known as Tau, causing it to aggregate, or group, in an insoluble form. These aggregations of hyperphosphorylated Tau protein are also referred to as PHFs, or "paired helical filaments". These aggregations are a histopathological feature not only of AD, but of many neurodegenerative diseases, which are collectively known as Tauopathies. Tauopathies include, e.g., Alzheimer's disease (AD), Pick's disease (PiD), progressive supranuclear palsy (PSP), corticobasal degeneration (CBD), and frontotemporal lobar degeneration (FTLD).

In addition to serving as markers for differential diagnosis and staging of the disease, Tau aggregates can also foster disease propagation. Therefore, diverse strategies for inhibiting Tau aggregation are being investigated as potential therapies against neurofibrillary lesion formation and disease progression. Several assays for in vitro formation of PHF have been described in the prior art (Friedhoff et al., Biochemistry 1998, 37: 10223-10230; Barghorn and Mandelkow, Biochemistry 2002, 41: 14885-14896; Morozova et al., Biochemistry 2013, 52:6960-6967). Thus, the assembly of Tau into filaments could be reproduced in vitro by adding compounds like polyanions, and fatty acids (and derivates). These methods however been shown to lack reproducibility and so far no reliable methods to prepare a homogenous population of Tau oligomers are available, hindering the ability to evaluate Tau oligomer toxicity and its possible role in the disease.

Therefore, there is still a need for novel and reliable methods which can be used, inter alia, for the testing of potential drugs which may interfere with the above described pathological Tau assembly, which may be useful for selecting new and effective drugs useful in the diagnosis and/or treatment of Tauopathies, such as AD.

SUMMARY OF THE INVENTION

In a first aspect, the present invention provides a method for the in vitro formation of paired helical filaments (PHF) of Tau protein, comprising incubating a mixture comprising a Tau protein preparation and a polyanionic co-factor for a pre-determined period of time under conditions that promote the formation of PHFs.

In a further aspect, the invention provides an in vitro method for detecting the formation of paired helical filaments (PHFs) of Tau protein, comprising the steps of:

(a) incubating a mixture comprising a Tau protein preparation and a polyanionic co-factor for a pre-determined period of time under conditions that promote the formation of PHFs; and (b) detecting the formed PHF by microscopial or spectroscopial means.

The invention further provides an in vitro method for the identification of a compound that is capable of inhibiting or promoting the formation of paired helical filaments of tauTau protein, comprising the steps of:

(a) performing a method as describe above in the absence and in the presence of a test compound; and (b) comparing the kinetics of the formation of PHFs in the absence of said test compound with the kinetics of the formation of PHFs in the presence of said test compound.

The present invention provides novel and reliable methods for the formation of and detection PHF which can be useful for the identification and selection of compounds that are capable of modulating, e.g. promoting or inhibiting pathological Tau-Tau protein association and pathological neurofilament aggregation. The methods of the present invention are particularly useful in screening compounds for the prophylaxis and treatment of Alzheimer's disease (AD).

DETAILED DESCRIPTION OF THE INVENTION

Figure 1:
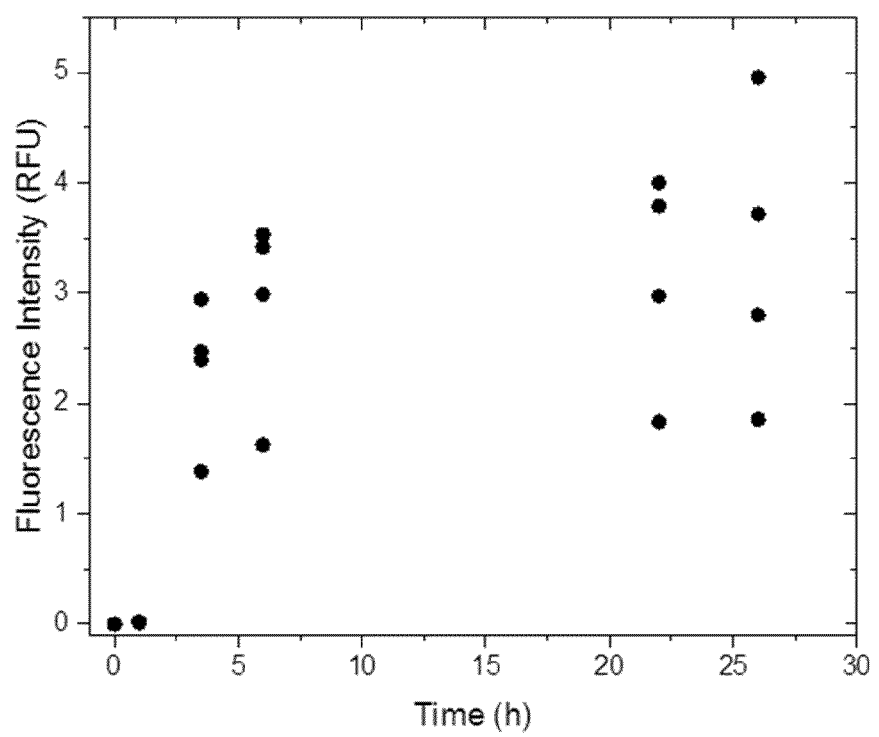
FIG. 1: Aggregation kinetics of rTau (15 μM, pH=7.4), monitored by ThT fluorescence spectroscopy. As shown, the data showed poor reproducibility (4 replicates).

NFTs are intraneuronal aggregates of the microtubule associated protein Tau formed by hyperphosphorylation of Tau protein, causing it to aggregate in an insoluble form. These aggregations of hyperphosphorylated Tau protein may also be referred to as "paired helical filaments" (PHFs). The precise mechanism of tangle formation is not completely understood, and whether tangles are a primary causative factor in the disease or play a more peripheral role is still a matter of debate. However, since PHFs are implicated in neurodegeneration it is of interest to reconstitute the aggregation process in vitro in the hope of understanding the underlying principles of aggregations and discovering means to prevent or reverse the process.

It is known that Tau aggregation follows a nucleation dependent polymerization (NDP) mechanism resulting in sigmoidal curves in which there are two different steps: a nucleation step (lag phase) and a growth phase (exponential growth after the lag phase) ending in an end plateau level of aggregation. The criteria for a NDP mechanism typically are the following:

Sigmoidal kinetics showing a lag phase followed by exponential growth;

Efficient seeding bypassing nucleation (i.e. when adding seeds an exponential growth should be observed and the lag phase is completely bypassed; and Concentration dependence.

According to the present invention, an in vitro assay for the formation of PHFs has been developed that displays the expected features of a nucleation dependent polymerization mechanism.

In a first aspect, the present invention thus provides an in vitro method for the formation of paired helical filaments (PHFs) of Tau protein, comprising incubating a Tau protein preparation and a polyanionic co-factor for a pre-determined period of time under conditions that promote the formation of PHFs.

In certain embodiments, the conditions that promote the formation of PHFs comprise shaking the incubation mixture at 350-500 cpm, preferably 400-450 cpm, in particular 425 cpm.

Tau proteins are derived from alternative mRNA splice variants that originate from a single gene and result in mature proteins that vary in size from 352 to 441 amino acids (36.8 to 45.9 kDa). There are six Tau iso forms, that differ from one another in having three or four microtubule binding repeats (R) of 31-32 amino acids each, and two, one or none amino terminal inserts (N) of 29 amino acids each. In certain embodiments, the Tau protein is full length recombinant Tau protein, preferably the longest iso form containing two N-terminal inserts and four microtubule binding domains, in particular Tau441.

In certain embodiments the Tau protein preparation is a substantially pure Tau preparation. A substantially pure Tau protein preparation as used herein refers to a Tau protein preparation that is at least 99% pure.

In certain embodiments, the concentration of Tau protein in the incubation mixture ranges between 10-30 µM, preferably between 12-20 µM. In certain embodiments, the concentration of Tau protein in the incubation mixture is 15 µM.

In certain embodiments, the Tau protein is in reduced form. This can be accomplished by adding a reducing agent to the incubating mixture, such as tris(2-carboxyethyl)phosphine) (TCEP). Alternatively, in certain embodiments, the Tau protein is a mutant recombinant Tau protein, wherein the cysteine residues are mutated. Thus, the Tau protein will remain in a reduced form, and no reducing agent is needed.

In certain embodiments, the incubation is performed at a pH of between 6.0 and 7.4, preferably between 6.5 and 7.0, more preferably at a pH of 6.7.

In certain embodiments, the incubation is performed at a temperature of between 36° C. and 38° C., preferably at a temperature of 37° C.

In certain embodiments, the polyanionic co-factor is heparin. In certain embodiments, the ratio of heparin:Tau protein is 1:2.

In certain embodiments, the pre-determined period of time is between 20 and 60 hours, preferably between 25 and 45 hours, in particular about 40 hours.

According to the present invention it has been found that by using a highly purified Tau protein preparation and optimized incubation conditions, Tau aggregation can be mimicked in vitro in a highly reproducible manner. The method of the invention displays the expected features of a nucleation dependent polymerization mechanism (lag phase followed by exponential growth and a stationary phase). The obtained aggregates display a PHF-like morphology, as confirmed by Atomic Force Microscopic images and are extremely efficient in seeding de novo aggregation of Tau.

The invention further provides an in vitro method for detecting the formation of paired helical filaments (PHFs) of Tau protein, comprising the steps of:

(a) incubating Tau protein and a polyanionic co-factor for a pre-determined period of time under conditions that promote the formation of PHFs; and (b) detecting the formed PHF by microscopial or spectroscopial means.

Several methods for detecting the formed PHF are known. According to the invention the detection of the formed PHF may be performed using microscopial means, such as electron microscopy (EM) or Atomic Force Microscopy (AFM), or spectroscopic means. In certain embodiments, the spectroscopic means comprises fluorescence spectroscopy, preferably thioflavin T fluorescence spectroscopy.

The present invention further provides an in vitro method for the identification of a compound that is capable of inhibiting or promoting the formation of paired helical filaments of Tau protein, comprising performing the method as described above both in the absence and in the presence of a test compound; and comparing the kinetics of the formation of PHFs in the absence of said test compound with the kinetics of the formation of PHFs in the presence of said test compound.

If the test compound inhibits the formation of PHFs the kinetics will be slower and be characterized by a longer lag phase and/or shallower growth phase and/or lower plateau.

If the test compound promotes the formation of PHFs the kinetics will have a shorter lag phase and/or a steeper growth phase and/or higher plateau.

The term "PHF formation "as used in accordance with this invention means the assembly or aggregation of Tau protein, or fragments thereof, into paired helical filaments. PHFs are characterized by a high order assembly of misfolded Tau molecules with fibrilar morphology.

The term "inhibiting the PHF formation" as used herein is not limited to (complete) "inhibiting" but also comprises "delaying" the PHF formation under suitable in vitro conditions.

According to the invention, a compound that is capable of promoting or inhibiting the PHF formation may be an antibody, or a derivative and/or fragment thereof.

Potential other inducers or inhibitors to be screened with the method of the present invention include small molecules which bind to, interfere with and/or occupy relevant sites on Tau. The present invention is particularly useful in assaying for potential PHF-formation inhibitors.

The present invention is further illustrated in the Examples, which are not intended to limit the invention in any way.

EXAMPLES

Example 1

In Vitro Aggregation Assay in Cuvette Format

Full length Tau was expressed in *E. coli* BL21 (DE3), purified by His-Trap affinity chromatography and stored in PBS pH=7.4 (in aliquots) at −80° C. Thioflavin T (ThT) stock solution 500 µM was prepared by dissolving the dried powder (Sigma-Aldrich, St Louis, Mo., USA) in PBS, pH 7.4, and filtered through a sterile 0.22 µm pore size PES membrane filter (Corning, N.Y., USA). The concentration was determined by absorbance measurements at 411 nm using an extinction coefficient of 22000 M−1 cm−1. Heparin stock solution was freshly prepared by dissolving the dried powder (Mw=17-19 kDa; Sigma-Aldrich, St Louis, Mo., USA) in PBS, pH 7.4, and filtered through a sterile 0.22 µm pore size PVDF membrane filter (Merck Millipore, Tullagreen, Cork, IRL).

Samples of 200 µl with a final ThT concentration of 25 µM, rTau 10-15 µM (concentration determined by absorbance measurements at 280 nm using an extinction coefficient of 0.31 ml mg−1 cm−1) and heparin in a ratio rTau: Hep=2:1 were incubated at 37° C. in 0.5 ml Eppendorf tubes with continuous shaking in a IKA Loopster digital rotor (15 rpm).

Figure 2:
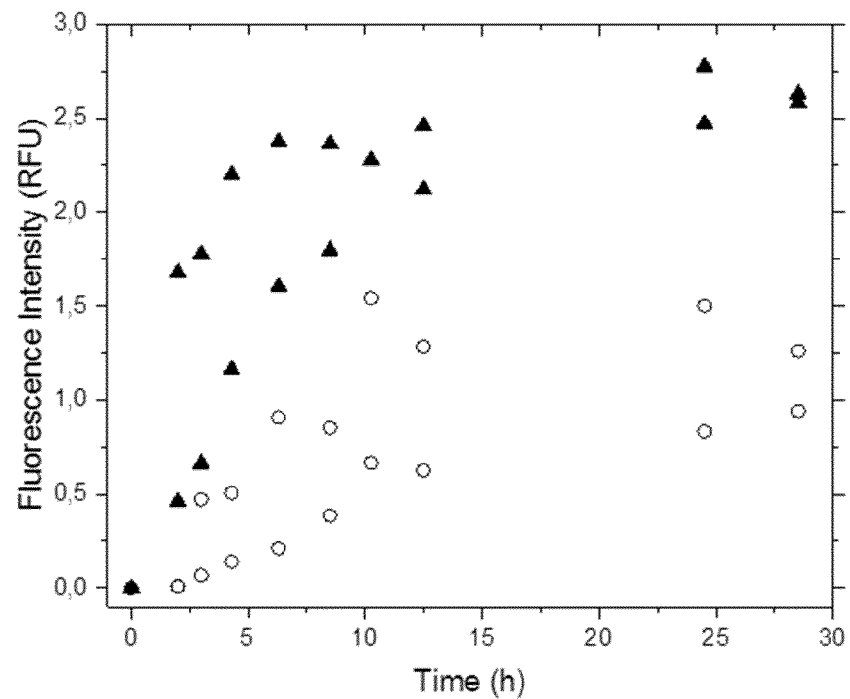
FIG. 2: Aggregation kinetics of rTau 10 μM (○) and 20 μM (▲), pH=7.4 monitored by ThT fluorescence spectroscopy. Data showed poor reproducibility (2 replicates of each concentration).
Figure 3:
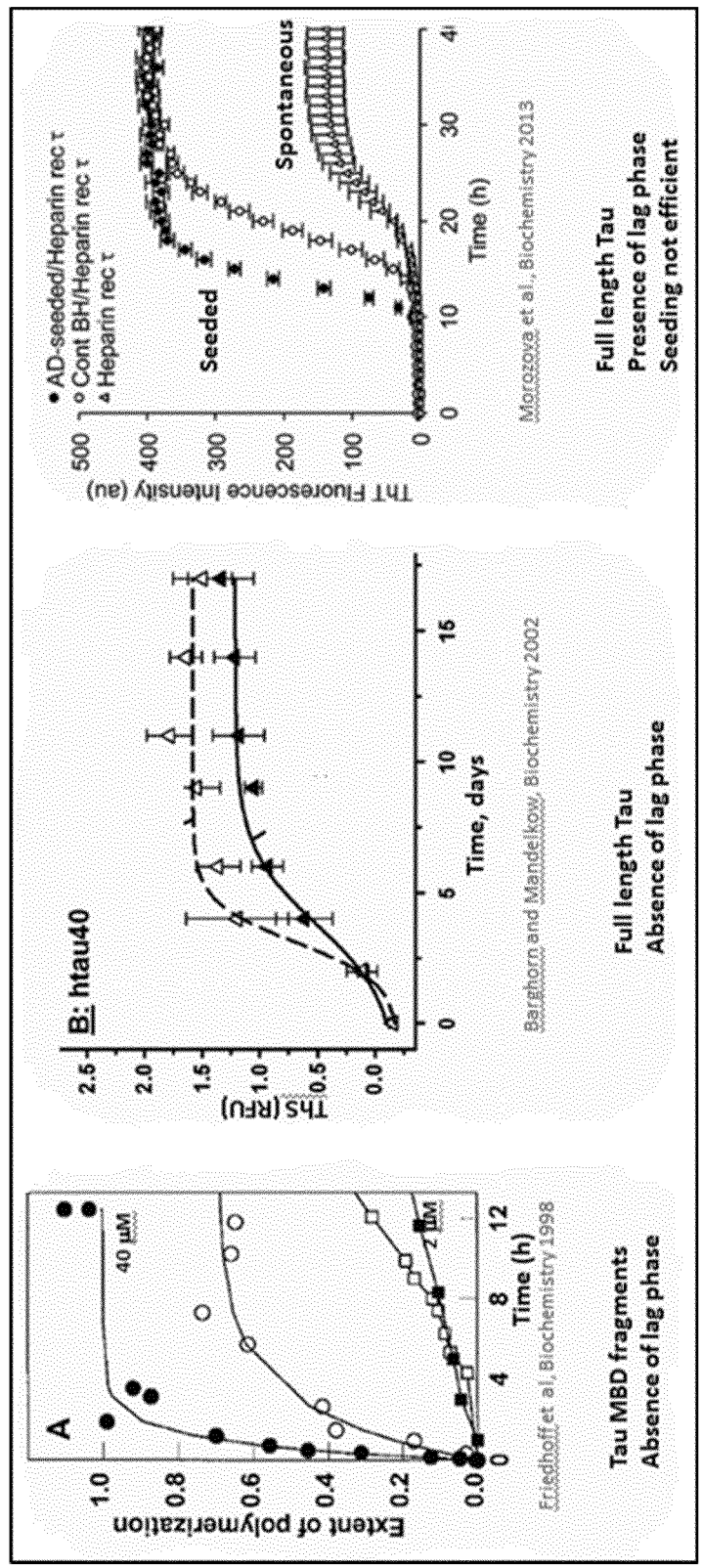
FIG. 3: Results from methods of the prior art.

Small amounts of the above described incubating reaction (10 µl) were taken periodically and mixed with ThT solution 25 µM in a final volume of 500 µl. ThT fluorescence kinetic measurements were carried out at 25° C. in quartz cells 5 mm light path (Hellma Analytics, Germany) in an ATF 105 Differential/Ratio Spectrofluorometer (Aviv, N.J., USA). Emission scans between 600-460 nm were recorded (maximum: 482 nm) for an excitation wavelength of 440 nm using a bandwidth of 4 nm and voltage 700/260 V. An irreproducibility in lag phase, growth and end plateau levels of aggregation was observed during fibrillization of rTau (FIGS. 1 and 2). The criteria for a Nucleation dependent polymerization (NDP) were not fulfilled. This was also observed in the literature (FIG. 3). Most of the published data refers to rTau fragments and no Full length rTau, which aggregate much faster. A general absence of reproducibility in the data was observed; sigmoidal kinetics without a well-defined lag phase followed by exponential growth or on the other hand, inefficient seeding were shown.

Figure 4:
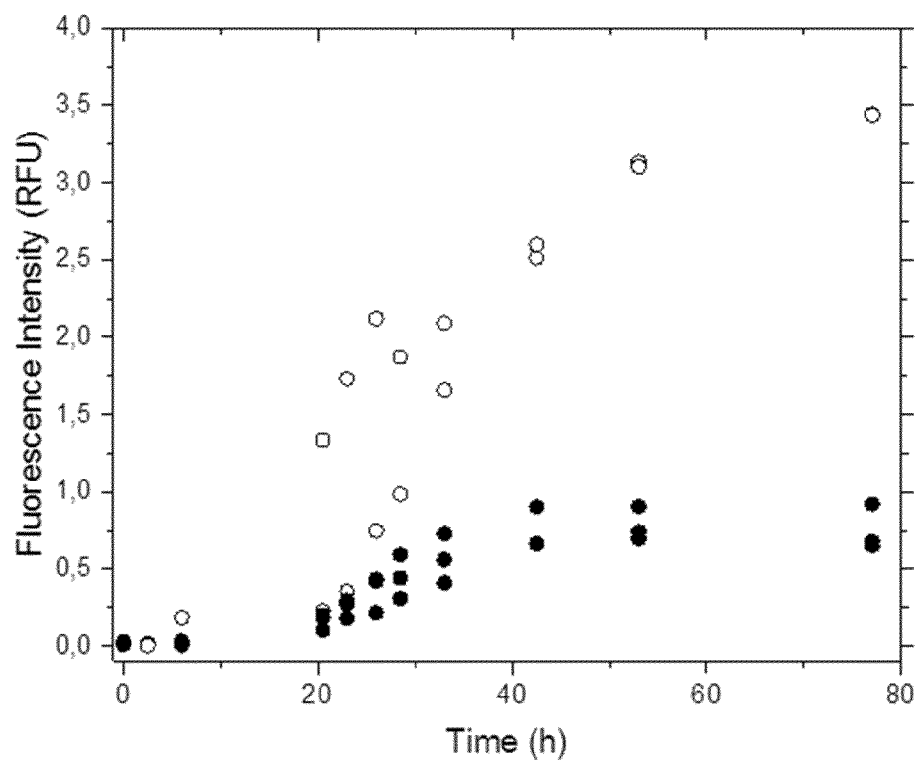
FIG. 4: Aggregation kinetics of 10 μM rTau in the absence (○) and presence (●) of 1 mM TCEP (3 replicates of each condition), monitored by ThT fluorescence spectroscopy.

The Tau molecule contains two cysteines that can form disulfide bridges resulting in different conformations that have a big impact in the aggregation kinetics. In order to reduce the disulfide bridges, a reducing agent, tris(2-carboxyethyl)phosphine (TCEP), was added to the protein solution. The kinetics of the aggregation process were followed by ThT fluorescence in the absence and presence of TCEP (FIG. 4).

The results in the presence of TCEP showed more reproducibility and different kinetic trends. In the absence of TCEP different behaviors were observed (variability between batches). Disulfide bridges can form compact monomer or dimers and when disulfide bridges are reduced, the Tau molecule is expected to be an open monomer. On one hand, the presence of compact monomers will extend the lag phase and also decrease end plateau level of aggregation. On the other hand, the presence of dimers will accelerate significantly the aggregation process. The combination of different molecular conformations may affect the end plateau level of aggregation.

Based on these results, it was decided to use a mutant tau protein (DCysM rTau), wherein the cysteine residues are mutated by substituting them by alanine.

Example 2

In Vitro Aggregation Assay in Plate Reader Format

Full length Tau double cysteine mutant (DCysM Tau) was expressed in *E. coli* BL21 (DE3), purified by His-Trap affinity chromatography and stored in PBS pH=7.4 (in aliquots) at −80° C. ThT fluorescence kinetic measurements were carried out at 37° C. in 96-well plates (Thermo Scientific, Vantaa, Finland) in a Biotek Synergy Neo2 Multi-Mode Microplate Reader (Biotek, Vt., USA) at an excitation wavelength of 440 nm and an emission wavelength of 485 nm.

Figure 5:
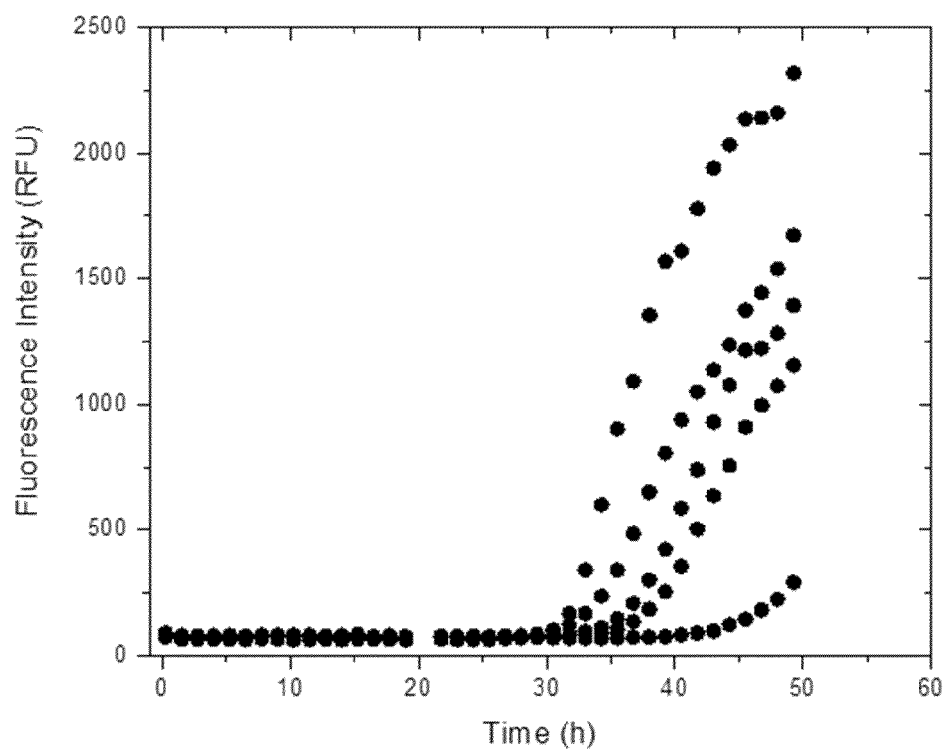
FIG. 5: Aggregation kinetics of rTau (DCysM rTau in PBS, frozen) 15 μM, pH=7.4 monitored by ThT fluorescence spectroscopy. Measurements were recorded using gain 60. Data showed poor reproducibility (5 replicates).
Figure 6:
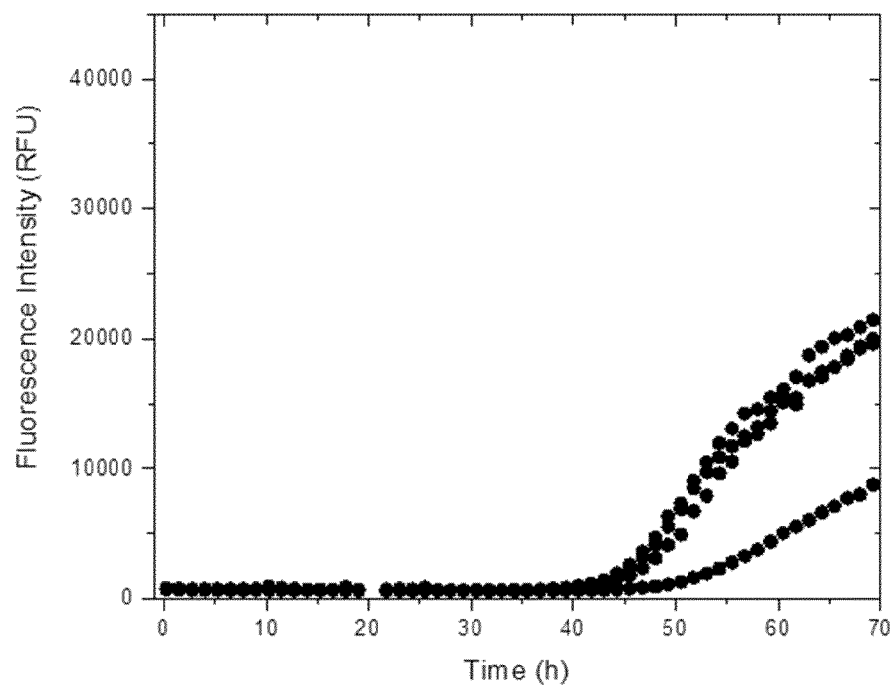
FIG. 6: Four replicates for the aggregation kinetics of rTau (DCysM rTau, frozen in PBS, pH 7.4) 15 μM measured by ThT fluorescence. Measurements were recorded using gain 80.
Figure 7:
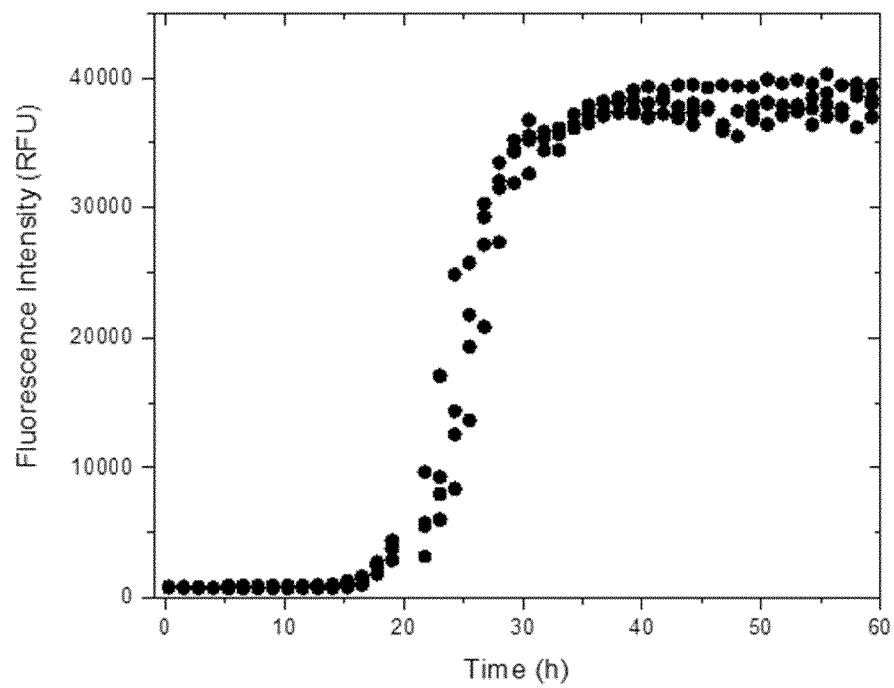
FIG. 7: Four replicates for the aggregation kinetics of rTau (DCysM rTau, lyophilized in PBS, 0.5 mM TCEP, pH 6.5) 15 μM measured by ThT fluorescence. Measurements were recorded using gain 80.
Figure 8:
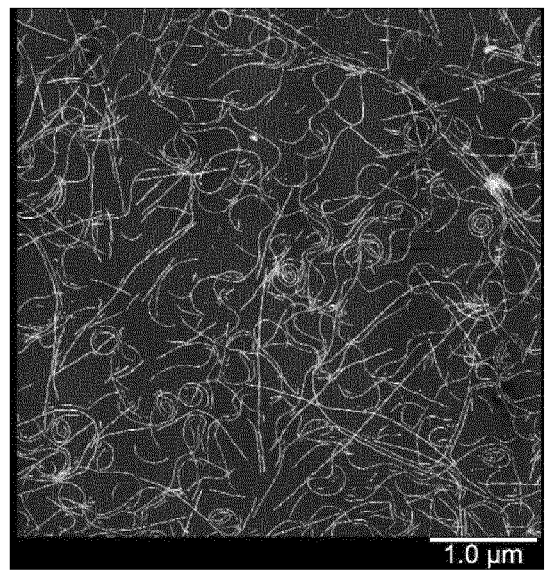
FIG. 8: AFM images for 15 µM DCysM rTau, lyophilized in PBS, 0.5 mM TCEP, pH 6.5. A: 1 µm zoom image; B: 300 nm zoom image.
Figure 8:
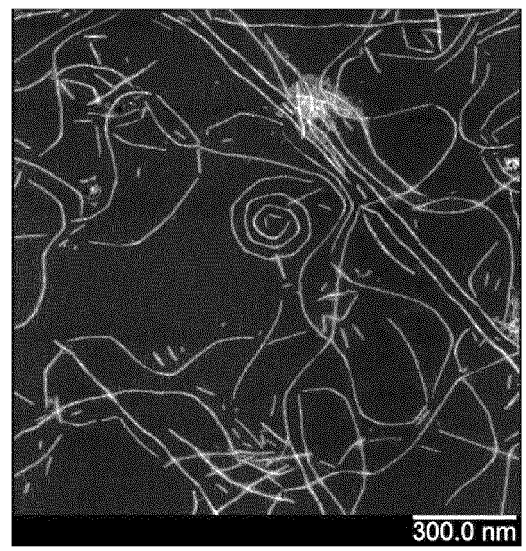
Figure 9:
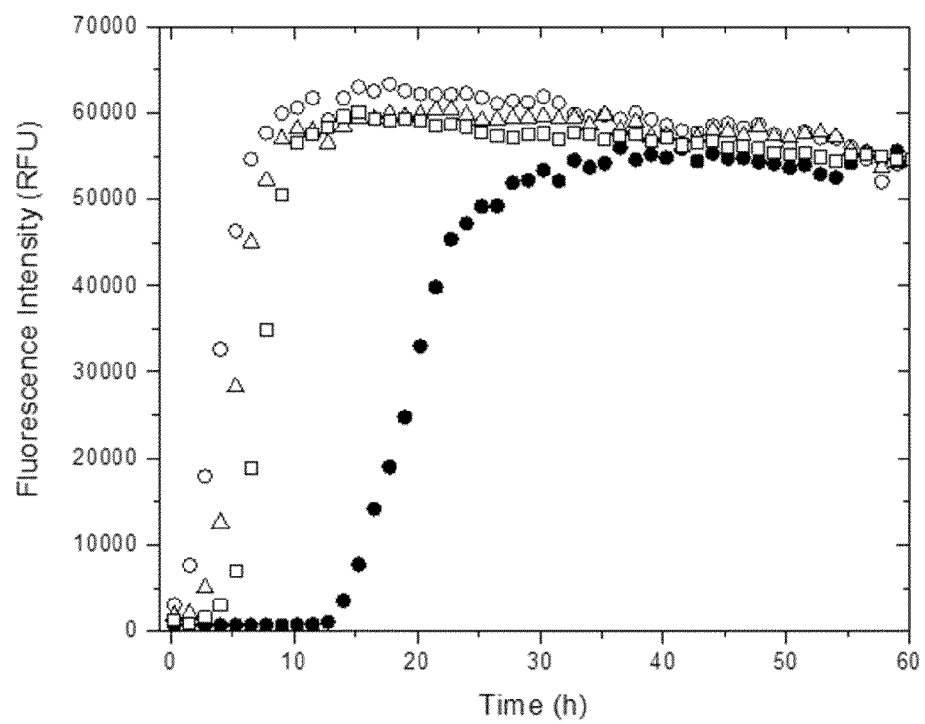
FIG. 9: Seeding data: aggregation kinetics for rTau (DCysM rTau in PBS, 0.5 mM TCEP, lyophilized) 15 µM, pH 6.5 measured by ThT fluorescence. Data is shown in the absence of seeds (●) or by adding 2.5% (○), 0.63% (Δ) or 0.16% (□) pre formed seeds, respectively.
Figure 10:
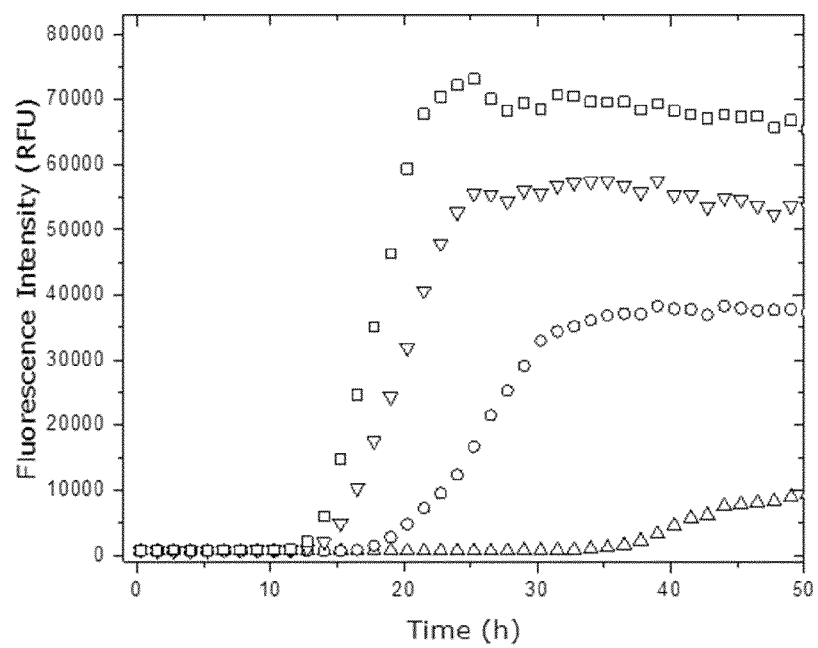
FIG. 10: Concentration dependence data: aggregation kinetics for rTau (DCysM rTau in PBS, 0.5 mM TCEP, lyophilized) 5 (Δ), 10 (○), 15 (v) and 20 µM (□), measured by ThT fluorescence. Measurements were recorded using gain 80. Critical concentration (minimum tau concentration required to have aggregation) was detected between 5 and 10 µM.

Samples of 200 µl with a final ThT concentration of 50 µM, heparin 8 µM and rTau 15 µM (concentration determined by absorbance measurements at 280 nm using an extinction coefficient of 0.31 ml mg−1 cm−1) were sealed with plate sealers (R&D Systems, Minneapolis, Minn.). Assay was optimized by assessing the effect of reducing agents and storing conditions for the starting rTau material (FIGS. 5 to 6). Data were recorded every 900 s, with continuous shaking (425 cpm, 3 mm). Final assay conditions fulfilling the NDP criteria are shown in FIG. 7-10:

- Sigmoidal kinetics showing a lag phase followed by exponential growth (FIG. 7)
- Aggregates display fibrillary structures (FIG. 8)
- Efficient seeding bypassing nucleation (when adding seeds an exponential growth should be observed in case or 100% compatibility between seeds and monomer; FIG. 9)
- Concentration dependence (FIG. 10)

Example 3

In Vitro Aggregation Assay in Plate Reader Format: Seeding rTau aggregated samples were pooled after 50 hand used as seeds for the de novo aggregation of rtau (FIG. 9). Addition of sonicated aggregates to fresh solutions of rTau generated a complete bypass of the lag phase observed in the spontaneous conversion of rTau (one of the strict criteria for a NDP mechanism).

Example 4

In Vitro Aggregation Assay in Plate Reader Format: Screening for Inhibitors

Figure 11:
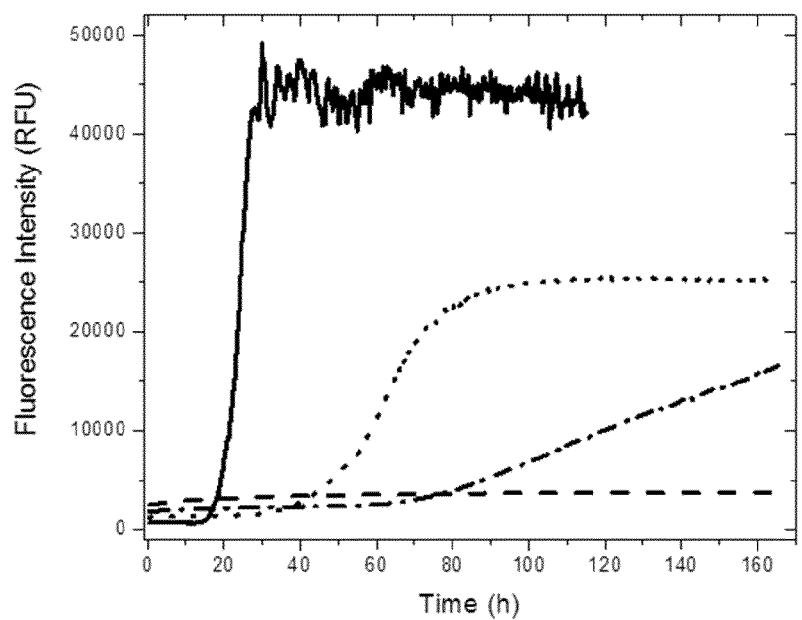
FIG. 11: Aggregation kinetics of rTau (DCysM rTau, pH 6.7) 15 µM measured by ThT fluorescence in the absence and presence of CBTAU 27.1 (rTau alone—straight line or with CBTAU-27.1 with concentration of 3 µM—dots; 6 µM—dash/dots; 9 µM—dash).

15 µM rTau was incubated either alone or in the presence of 3, 6 and 9 µM CBTAU 27.1 (a tau binding antibody) in a 200 µl PBS solution containing 50 µM ThT, 8 µM heparin and 0.5 mM TCEP. The plate was sealed with plate sealers (R&D Systems, Minneapolis, Minn.) and measurements were recorded every 900 s, with continuous shaking (425 cpm, 3 mm), see FIG. 11. It can be observed that in the presence of 9 µM CBTAU-27.1, the conversion of rtau is completely blocked for the entire duration of the assay (160 hrs). In the presence of 6 µM CBTAU-27.1 the lag phase of the conversion was extended to 70 hrs and the conversion was not completed in the 160 hr assay interval. 3 µM CBTAU-27.1 is also inhibiting the conversion of rtau which is emphasized by a longer lag phase and a lower final plateau.

The invention claimed is:

1. A method for the in vitro formation of paired helical filaments (PHFs) of Tau protein that displays the features of a nucleation dependent polymerization mechanism, comprising incubating a mixture comprising a Tau protein preparation and a polyanionic co-factor for a pre-determined period of time under conditions that promote the formation of PHFs wherein the Tau protein is a mutant recombinant Tau protein, wherein the cysteine residues are mutated.

2. The method according to claim 1, wherein the conditions that promote the formation of PHFs comprise shaking the incubation mixture at 350-500 cpm.

3. The method according to claim 1, wherein the Tau protein is a full length recombinant Tau protein.

4. The method according to claim 3, wherein the polyanionic co-factor is heparin.

5. The method according to claim 1, wherein the Tau protein preparation is a substantially pure Tau preparation.

6. The method according to claim 1, wherein a concentration of Tau protein in the incubation mixture ranges between 10 µM and 30 µM.

7. The method according to claim 1, wherein the Tau protein is in a reduced form.

8. The method according to claim 1, wherein the incubation is performed at a pH of between 6.0 and 7.4.

9. The method according to claim 1, wherein the incubation is performed at a temperature of between 36° C. and 38° C.

10. The method according to claim 1, wherein the polyanionic co-factor is heparin.

11. An in vitro method for detecting the formation of paired helical filaments (PHFs) of Tau protein, comprising the steps of:
    (a) inducing the formation of PHFs using a method according to claim 1; and
    (b) detecting the formed PHF by microscopic or spectroscopic means.

12. The method according to claim 11, wherein the spectroscopic means comprises fluorescence spectroscopy.

13. An in vitro method for the identification of a compound that is capable of inhibiting or promoting the formation of paired helical filaments of Tau protein, comprising the steps of:
    (a) performing the method according to claim 10 in the absence and in the presence of a test compound; and
    (b) comparing the kinetics of the formation of PHFs in the absence of said test compound with the kinetics of the formation of PHFs in the presence of said test compound.

14. The method according to claim 13, wherein the compound is an antibody or fragment thereof.

15. The method according to claim 13, wherein the polyanionic co-factor is heparin.

16. The method according to claim 11, wherein the spectroscopic means comprises a thioflavin T fluorescence assay.

17. The method according to claim 11, wherein the polyanionic co-factor is heparin.

18. The method according to claim 1, wherein the conditions that promote the formation of PHFs comprise shaking the incubation mixture at 400-450 cpm.

19. The method according to claim 1, wherein the Tau protein is a full length recombinant Tau protein containing two N-terminal inserts and four microtubule binding domains.

20. The method according to claim 1, wherein a concentration of Tau protein in the incubation mixture ranges between 12 µM and 20 µM.

* * * * *